(12) United States Patent
Metzner et al.

(10) Patent No.: US 10,792,427 B2
(45) Date of Patent: Oct. 6, 2020

(54) HIGH FORCE INJECTION DEVICES

(71) Applicant: Allergan, Inc., Irvine, CA (US)

(72) Inventors: Jason S. Metzner, Covington, WA (US); Zachary Dominguez, Santa Barbara, CA (US); Justin J. Schwab, San Francisco, CA (US); Ethan Franklin, Goleta, CA (US); Mike Augarten, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 91 days.

(21) Appl. No.: 16/020,951

(22) Filed: Jun. 27, 2018

(65) Prior Publication Data

US 2018/0304013 A1 Oct. 25, 2018

Related U.S. Application Data

(63) Continuation of application No. 14/702,581, filed on May 1, 2015, now Pat. No. 10,029,048.

(60) Provisional application No. 61/992,380, filed on May 13, 2014.

(51) Int. Cl.
*A61M 5/20* (2006.01)
*A61M 5/315* (2006.01)

(52) U.S. Cl.
CPC ............ *A61M 5/20* (2013.01); *A61M 5/2046* (2013.01); *A61M 5/31515* (2013.01); *A61M 5/31576* (2013.01); *A61M 2005/2026* (2013.01); *A61M 2005/3152* (2013.01); *A61M 2005/31588* (2013.01); *A61M 2205/502* (2013.01); *A61M 2205/52* (2013.01)

(58) Field of Classification Search
CPC .. A61M 2205/8218; A61M 2205/8225; A61M 2205/8231; A61M 2005/14204; A61M 5/155; A61M 5/2046; A61M 5/2053; A61M 5/30
See application file for complete search history.

(56) References Cited

U.S. PATENT DOCUMENTS

| | | | |
|---|---|---|---|
| 1,250,114 A | 12/1917 | Bigelow et al. |
| 1,558,037 A | 10/1925 | Morton |
| 1,591,021 A | 7/1926 | Davis |
| 2,007,140 A | 7/1935 | Ragnar |
| 2,302,986 A | 11/1942 | Vollrath |
| 2,491,978 A | 12/1949 | Helfman |
| 2,551,902 A | 5/1951 | Rieck |

(Continued)

FOREIGN PATENT DOCUMENTS

| | | |
|---|---|---|
| CN | 2535071 | 2/2003 |
| CN | 200960353 | 10/2007 |

(Continued)

OTHER PUBLICATIONS

Bleyer, "SIS Facial Implant 510(k) Summary," Cook Biotech Inc. May 2005.

(Continued)

*Primary Examiner* — Emily L Schmidt
(74) *Attorney, Agent, or Firm* — Nathan S. Smith; Sujohn Das; Morgan, Lewis & Bockius LLP

(57) ABSTRACT

Described herein are assisted syringes. The syringes provide a higher force to the plunger tip than the extrusion force applied to the plunger. The assisted syringes can be used to inject or extrude viscous materials.

16 Claims, 6 Drawing Sheets

(56) References Cited

U.S. PATENT DOCUMENTS

| | | |
|---|---|---|
| 2,737,946 A | 3/1956 | Hein, Jr. |
| 2,853,070 A | 9/1958 | Julliard |
| 3,086,530 A | 4/1963 | Groom |
| 3,161,323 A | 12/1964 | Bent |
| D202,754 S | 11/1965 | Fnftolin |
| D214,112 S | 5/1969 | Langdon |
| 3,517,668 A | 6/1970 | Brickson |
| 3,595,231 A | 7/1971 | Pistor |
| D224,066 S | 6/1972 | McDonald |
| 3,688,765 A * | 9/1972 | Gasaway ............... A61M 5/30 604/70 |
| 3,720,211 A | 3/1973 | Kyrias |
| 3,767,085 A | 10/1973 | Cannon et al. |
| 3,807,048 A | 4/1974 | Malmin |
| 3,910,282 A | 10/1975 | Messer et al. |
| 3,916,777 A | 11/1975 | Earl |
| 4,064,879 A | 12/1977 | Leibinsohn |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,346,708 A | 8/1982 | Leeven |
| 4,444,560 A | 4/1984 | Jacklich |
| 4,529,401 A | 7/1985 | Leslie et al. |
| 4,605,691 A | 8/1986 | Balazs et al. |
| 4,617,016 A | 10/1986 | Blomberg |
| 4,624,659 A | 11/1986 | Goldberg |
| 4,627,444 A | 12/1986 | Brooker |
| 4,671,255 A | 6/1987 | Dubrul et al. |
| 4,695,273 A | 9/1987 | Brown |
| 4,699,612 A | 10/1987 | Hamacher |
| 4,710,172 A | 12/1987 | Jacklich |
| 4,719,918 A | 1/1988 | Bonomo et al. |
| 4,755,169 A | 7/1988 | Samoff |
| 4,759,750 A | 7/1988 | Devries |
| 4,800,901 A | 1/1989 | Rosenberg |
| 4,832,692 A | 5/1989 | Box |
| 4,841,948 A | 6/1989 | Bauser et al. |
| 4,841,992 A | 6/1989 | Sasaki et al. |
| 4,846,886 A | 7/1989 | Fey et al. |
| D303,010 S | 8/1989 | Jabbusch |
| 4,869,717 A | 9/1989 | Adair |
| 4,908,029 A | 3/1990 | Bark et al. |
| 4,909,932 A | 3/1990 | Monnet |
| 4,955,905 A | 9/1990 | Reed |
| 4,957,744 A | 9/1990 | dellaValle et al. |
| 4,898,572 A | 12/1990 | Surugue nee Lasnier |
| 5,024,613 A | 6/1991 | Vasconcellos |
| 5,024,656 A | 6/1991 | Gasaway et al. |
| 5,046,506 A | 9/1991 | Singer |
| 5,066,303 A | 11/1991 | Bark et al. |
| 5,092,348 A | 3/1992 | Dubrul et al. |
| 5,100,390 A | 3/1992 | Lubeck et al. |
| 5,104,375 A | 3/1992 | Lubeck et al. |
| 5,116,358 A | 5/1992 | Granger et al. |
| 5,127,436 A | 7/1992 | Campion et al. |
| 5,137,181 A | 8/1992 | Keller |
| 5,141,496 A | 8/1992 | Dalto et al. |
| 5,211,644 A | 5/1993 | VanBeek et al. |
| 5,258,013 A | 11/1993 | Granger et al. |
| 5,270,685 A | 12/1993 | Hagen |
| 5,279,544 A | 1/1994 | Gross |
| 5,295,980 A | 3/1994 | Ersek |
| 5,305,788 A | 4/1994 | Mayeux |
| 5,318,544 A | 6/1994 | Drypen |
| 5,322,511 A | 6/1994 | Armbruster et al. |
| 5,344,407 A | 9/1994 | Ryan |
| 5,354,279 A | 10/1994 | Hofling |
| 5,368,572 A | 11/1994 | Shirota |
| 5,383,851 A | 1/1995 | Mackinnon, Jr. |
| 5,405,330 A | 4/1995 | Zunitch et al. |
| 5,433,352 A | 7/1995 | Ronvig |
| 5,478,327 A | 12/1995 | McGregor et al. |
| 5,520,658 A | 5/1996 | Holm |
| 5,540,657 A | 7/1996 | Kurjan |
| 5,549,672 A | 8/1996 | Maddock et al. |
| 5,584,815 A | 12/1996 | Pawelka et al. |
| 5,611,809 A | 3/1997 | Marshall et al. |
| D378,939 S | 4/1997 | Smith et al. |
| 5,650,317 A | 7/1997 | Chang et al. |
| 5,690,618 A | 11/1997 | Smith et al. |
| 5,716,404 A | 2/1998 | Vacanti |
| 5,722,829 A | 3/1998 | Wilcox et al. |
| 5,728,077 A | 3/1998 | Williams |
| 5,752,970 A | 5/1998 | Yoon |
| 5,807,340 A | 9/1998 | Pokras |
| 5,814,511 A | 9/1998 | Chang et al. |
| 5,817,033 A | 10/1998 | DeSantis |
| 5,824,335 A | 10/1998 | Dorigatti et al. |
| 5,846,225 A | 12/1998 | Rosengart et al. |
| 5,853,388 A | 12/1998 | Semel |
| 5,941,845 A | 8/1999 | Tu et al. |
| 5,964,737 A | 10/1999 | Caizza |
| 5,972,385 A | 10/1999 | Liu et al. |
| 6,047,861 A | 4/2000 | Vidal et al. |
| D424,194 S | 5/2000 | Holdaway et al. |
| 6,077,251 A | 6/2000 | Ting et al. |
| 6,082,364 A | 7/2000 | Balian et al. |
| 6,083,912 A | 7/2000 | Khouri |
| 6,102,929 A | 8/2000 | Conway et al. |
| 6,129,761 A | 10/2000 | Hubbell et al. |
| 6,159,233 A | 12/2000 | Matsuzawa |
| 6,171,276 B1 | 1/2001 | Lippe |
| 6,171,610 B1 | 1/2001 | Vacanti et al. |
| 6,176,396 B1 | 1/2001 | Hamada et al. |
| 6,183,434 B1 | 2/2001 | Eppstein |
| D441,077 S | 4/2001 | Garito et al. |
| 6,214,045 B1 | 4/2001 | Corbitt, Jr. et al. |
| 6,231,552 B1 | 5/2001 | Jentzen |
| 6,231,570 B1 | 5/2001 | Tu et al. |
| 6,239,105 B1 | 5/2001 | Brewitt et al. |
| 6,283,951 B1 | 9/2001 | Flaherty et al. |
| 6,293,925 B1 | 9/2001 | Safabash et al. |
| 6,303,518 B1 | 10/2001 | Aceti |
| 6,312,412 B1 | 11/2001 | Saied |
| 6,316,247 B1 | 11/2001 | Katz |
| 6,406,455 B1 * | 6/2002 | Willis ................ A61M 5/30 604/191 |
| 6,432,046 B1 | 8/2002 | Yarush et al. |
| 6,451,240 B1 | 9/2002 | Sherman et al. |
| 6,482,187 B1 | 11/2002 | Gibbs |
| 6,488,651 B1 | 12/2002 | Morris |
| 6,551,290 B1 | 4/2003 | Elsberry et al. |
| 6,582,960 B1 | 6/2003 | Martin et al. |
| 6,595,960 B2 | 7/2003 | West et al. |
| 6,607,512 B2 | 8/2003 | Oliver |
| 6,607,513 B1 | 8/2003 | Down |
| 6,610,033 B1 | 8/2003 | Melanson et al. |
| 6,611,707 B1 | 8/2003 | Prausnitz et al. |
| 6,613,010 B2 | 9/2003 | Castellano |
| 6,616,448 B2 | 9/2003 | Friedman |
| 6,638,308 B2 | 10/2003 | Corbitt |
| D483,116 S | 12/2003 | Castellano |
| 6,656,488 B2 | 12/2003 | Yi et al. |
| 6,666,893 B2 | 12/2003 | Burg et al. |
| 6,689,095 B1 | 2/2004 | Garitano et al. |
| 6,689,103 B1 | 2/2004 | Palasis |
| 6,777,231 B1 | 8/2004 | Katz et al. |
| 6,780,171 B2 | 8/2004 | Gabel |
| 6,783,514 B2 | 8/2004 | Tovey et al. |
| 6,824,526 B2 | 11/2004 | Castellano |
| 6,881,226 B2 | 4/2005 | Corbitt |
| 6,896,666 B2 | 5/2005 | Kochamba |
| 6,901,850 B2 | 6/2005 | Corominas |
| 6,908,453 B2 | 6/2005 | Fleming |
| 6,916,603 B2 | 7/2005 | Baron et al. |
| 6,936,297 B2 | 8/2005 | Roby et al. |
| 6,945,952 B2 | 9/2005 | Kwon |
| 6,991,652 B2 | 1/2006 | Burg et al. |
| 7,004,928 B2 | 2/2006 | Aceti |
| 7,015,037 B1 | 3/2006 | Furcht et al. |
| 7,018,356 B2 | 3/2006 | Wise et al. |
| 7,033,337 B2 | 4/2006 | Hjertman |
| 7,041,088 B2 | 5/2006 | Nawrocki et al. |

(56) References Cited

U.S. PATENT DOCUMENTS

| | | |
|---|---|---|
| 7,047,070 B2 | 5/2006 | Wilkinson et al. |
| 7,048,729 B2 | 5/2006 | Meglin et al. |
| 7,097,631 B2 | 8/2006 | Trautman |
| 7,108,681 B2 | 9/2006 | Gartstein |
| 7,115,108 B2 | 10/2006 | Wilkinson et al. |
| 7,129,209 B2 | 10/2006 | Rhee et al. |
| 7,150,726 B2 | 12/2006 | Dalton |
| 7,285,266 B2 | 10/2007 | Voumakis et al. |
| 7,302,885 B2 | 12/2007 | Townsend |
| 7,316,822 B2 | 1/2008 | Binette et al. |
| 7,361,163 B2 | 4/2008 | Cohen |
| 7,390,484 B2 | 6/2008 | Fraser |
| 7,419,472 B2 | 9/2008 | Hibner et al. |
| 7,442,187 B2 | 10/2008 | Khayal et al. |
| 7,445,793 B2 | 11/2008 | Niwa et al. |
| 7,494,473 B2 | 2/2009 | Eggers et al. |
| 7,501,115 B2 | 3/2009 | Fraser et al. |
| 7,504,386 B2 | 3/2009 | Pressato et al. |
| 7,514,075 B2 | 4/2009 | Hedrick et al. |
| 7,556,615 B2 | 7/2009 | Pettis et al. |
| 7,559,952 B2 | 7/2009 | Pinchuck |
| 7,560,276 B2 | 7/2009 | Harmon et al. |
| 7,588,547 B2 | 9/2009 | Deem |
| 7,611,495 B1 | 11/2009 | Gianturco |
| 7,651,475 B2 | 1/2010 | Angel |
| 7,651,684 B2 | 1/2010 | Hedrick et al. |
| 7,662,110 B2 | 2/2010 | Flaherty |
| 7,664,545 B2 | 2/2010 | Westersten et al. |
| 7,666,339 B2 | 2/2010 | Chaouk et al. |
| D615,192 S | 5/2010 | Mudd et al. |
| 7,722,582 B2 | 5/2010 | Lina et al. |
| 7,762,983 B2 | 7/2010 | Arnissolle |
| 7,767,452 B2 | 8/2010 | Kleinsek et al. |
| 7,799,767 B2 | 9/2010 | Lamberti et al. |
| 7,850,656 B2 | 12/2010 | McKay et al. |
| 7,850,683 B2 | 12/2010 | Elkins |
| 7,875,296 B2 | 1/2011 | Binette et al. |
| 7,878,981 B2 | 2/2011 | Strother et al. |
| 7,896,837 B2 | 3/2011 | Wilkinson et al. |
| D637,287 S | 5/2011 | Mudd et al. |
| 7,998,170 B2 | 8/2011 | Cunningham |
| 8,012,139 B2 | 9/2011 | McKay et al. |
| 8,029,460 B2 | 10/2011 | Rush et al. |
| 8,053,423 B2 | 11/2011 | Lamberti et al. |
| 8,066,629 B2 | 11/2011 | Dlugos |
| 8,066,691 B2 | 11/2011 | Khouri |
| 8,083,722 B2 | 12/2011 | McKay et al. |
| 8,088,108 B2 | 1/2012 | Kraft |
| 8,137,705 B2 | 3/2012 | Doyle et al. |
| 8,153,591 B2 | 4/2012 | Masters et al. |
| 8,157,830 B2 | 4/2012 | Wenchell |
| 8,172,815 B2 | 5/2012 | Down et al. |
| 8,216,190 B2 | 7/2012 | Gartstein |
| 8,236,021 B2 | 8/2012 | Kluge |
| 8,291,768 B2 | 10/2012 | Spiegel |
| 8,303,518 B2 | 11/2012 | Aceti |
| 8,303,545 B2 | 11/2012 | Schraga |
| 8,343,132 B2 | 1/2013 | Heneveld et al. |
| 8,349,554 B2 | 1/2013 | Bahrami et al. |
| 8,353,871 B2 | 1/2013 | Zimmerman |
| 8,366,643 B2 | 2/2013 | Deem |
| 8,394,118 B2 | 3/2013 | Jones et al. |
| 8,409,147 B2 | 4/2013 | Kraft |
| 8,409,185 B2 | 4/2013 | Burger |
| 8,480,630 B2 | 7/2013 | Mudd et al. |
| 8,535,278 B2 | 9/2013 | Mudd et al. |
| 8,562,571 B2 | 10/2013 | Mudd et al. |
| 8,603,028 B2 | 12/2013 | Mudd et al. |
| 8,632,501 B2 | 1/2014 | Kraft |
| 8,636,797 B2 | 1/2014 | Chitre et al. |
| 8,657,786 B2 | 2/2014 | Bahrami et al. |
| 8,668,675 B2 | 3/2014 | Chase |
| 8,708,965 B2 | 4/2014 | Boyden |
| 8,712,815 B1 | 4/2014 | Nichols et al. |
| 8,821,446 B2 | 9/2014 | Trautman |
| 8,900,181 B2 | 12/2014 | Knowlton |
| 8,900,186 B2 | 12/2014 | Pettis et al. |
| 8,945,060 B2 | 2/2015 | Bunch |
| 9,017,289 B2 | 4/2015 | Backes |
| 9,017,318 B2 | 4/2015 | Fourkas |
| 9,039,688 B2 | 5/2015 | Palmer, III |
| 9,066,712 B2 | 6/2015 | Fourkas |
| 9,072,498 B2 | 7/2015 | Elkins |
| 9,101,346 B2 | 8/2015 | Burger |
| 9,113,855 B2 | 8/2015 | Burger |
| 9,149,331 B2 | 10/2015 | Deem |
| 9,155,584 B2 | 10/2015 | Fourkas |
| 9,180,273 B2 | 11/2015 | Konstantino |
| 9,214,030 B2 | 12/2015 | Sole et al. |
| 9,227,023 B2 | 1/2016 | Kraft |
| 9,241,753 B2 | 1/2016 | Fourkas |
| 9,254,162 B2 | 2/2016 | Burger |
| 9,289,605 B2 | 3/2016 | Choi |
| 9,314,568 B2 | 4/2016 | Gurtner et al. |
| 9,468,748 B2 | 10/2016 | Bang |
| 2001/0008937 A1 | 7/2001 | Callegaro et al. |
| 2002/0010433 A1 | 1/2002 | Johnson |
| 2002/0026039 A1 | 2/2002 | Bellini et al. |
| 2002/0065483 A1 | 5/2002 | Leon |
| 2002/0133114 A1 | 9/2002 | Itoh |
| 2002/0151843 A1 | 10/2002 | Correa et al. |
| 2003/0028154 A1 | 2/2003 | Ros |
| 2003/0050602 A1 | 3/2003 | Pettis et al. |
| 2003/0078912 A1 | 4/2003 | Oliver |
| 2003/0144632 A1 | 7/2003 | Hommann et al. |
| 2003/0181863 A1 | 9/2003 | Ackley |
| 2003/0199883 A1 | 10/2003 | Laks |
| 2003/0233067 A1 | 12/2003 | McIntosh et al. |
| 2004/0010224 A1 | 1/2004 | Bodmeier |
| 2004/0015133 A1 | 1/2004 | Karim |
| 2004/0092011 A1 | 5/2004 | Wilkison et al. |
| 2004/0092927 A1 | 5/2004 | Podhajsky et al. |
| 2004/0147883 A1 | 7/2004 | Tsai |
| 2004/0192643 A1 | 9/2004 | Pressato et al. |
| 2004/0220532 A1 | 11/2004 | Caizza |
| 2005/0025755 A1 | 2/2005 | Hedrick |
| 2005/0033362 A1 | 2/2005 | Grafton |
| 2005/0085767 A1 | 4/2005 | Menassa |
| 2005/0123895 A1 | 6/2005 | Freund |
| 2005/0131353 A1 | 6/2005 | Mossanen-Shams et al. |
| 2005/0137496 A1 | 7/2005 | Walsh et al. |
| 2005/0147562 A1 | 8/2005 | Hunter et al. |
| 2005/0177117 A1 | 8/2005 | Crocker et al. |
| 2005/0182446 A1 | 8/2005 | DeSantis |
| 2005/0215956 A1 | 9/2005 | Nerney |
| 2005/0261633 A1 | 11/2005 | Khalaj |
| 2006/0041320 A1 | 2/2006 | Matsuda |
| 2006/0079765 A1 | 4/2006 | Neer |
| 2006/0089594 A1 | 4/2006 | Landau |
| 2006/0150742 A1 | 7/2006 | Esnouf |
| 2007/0038181 A1 | 2/2007 | Melamud |
| 2007/0083155 A1 | 4/2007 | Muller |
| 2007/0085767 A1 | 4/2007 | Jung et al. |
| 2007/0100363 A1 | 5/2007 | Dollar et al. |
| 2007/0167920 A1 | 7/2007 | Hommann |
| 2007/0191781 A1 | 8/2007 | Richards et al. |
| 2007/0212385 A1 | 9/2007 | David |
| 2007/0250010 A1 | 10/2007 | Hohlfelder et al. |
| 2007/0251531 A1 | 11/2007 | Khouri |
| 2007/0270710 A1 | 11/2007 | Frass et al. |
| 2008/0015522 A1 | 1/2008 | Yeshurun |
| 2008/0033347 A1 | 2/2008 | D'Arrigo et al. |
| 2008/0058706 A1 | 3/2008 | Zhang |
| 2008/0058839 A1 | 3/2008 | Nobles |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0119797 A1 | 5/2008 | Kim |
| 2008/0119876 A1 | 5/2008 | Price et al. |
| 2008/0161772 A1 | 7/2008 | Nayak |
| 2008/0167674 A1 | 7/2008 | Bodduluri et al. |
| 2008/0188816 A1 | 8/2008 | Shimazaki |
| 2008/0200758 A1 | 8/2008 | Orbay et al. |

(56) References Cited

U.S. PATENT DOCUMENTS

| | | |
|---|---|---|
| 2008/0243028 A1 | 10/2008 | Howard et al. |
| 2008/0281278 A1 | 11/2008 | Williams |
| 2008/0299213 A2 | 12/2008 | Kleinsek |
| 2008/0317718 A1 | 12/2008 | Yoshimura |
| 2009/0088703 A1 | 4/2009 | Azar |
| 2009/0098177 A1 | 4/2009 | Werkmeister et al. |
| 2009/0123547 A1 | 5/2009 | Hill |
| 2009/0124552 A1 | 5/2009 | Hill |
| 2009/0124996 A1 | 5/2009 | Heneveld et al. |
| 2009/0125050 A1 | 5/2009 | Dixon |
| 2009/0131886 A1 | 5/2009 | Liu et al. |
| 2009/0143746 A1 | 6/2009 | Mudd et al. |
| 2009/0162415 A1 | 6/2009 | Huang et al. |
| 2009/0187118 A1 | 7/2009 | Kim |
| 2009/0234322 A1 | 9/2009 | Fischer |
| 2009/0240200 A1 | 9/2009 | Heneveld et al. |
| 2009/0246182 A1 | 10/2009 | Casteilla |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2009/0312746 A1 | 12/2009 | Khouri |
| 2009/0317367 A1 | 12/2009 | Chazenbalk |
| 2010/0006095 A1 | 1/2010 | Woodcock |
| 2010/0010627 A1 | 1/2010 | Matheny |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1 | 5/2010 | Lockard |
| 2010/0152675 A1 | 6/2010 | McClintock |
| 2010/0152679 A1 | 6/2010 | Tezel |
| 2010/0179488 A1 | 7/2010 | Spiegel |
| 2010/0256594 A1 | 10/2010 | Kimmell |
| 2010/0256596 A1 | 10/2010 | Chomas |
| 2010/0279405 A1 | 11/2010 | Peterson |
| 2010/0280488 A1 | 11/2010 | Pruiitt et al. |
| 2010/0282774 A1 | 11/2010 | Greter et al. |
| 2010/0286618 A1 | 11/2010 | Choi |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0070281 A1 | 3/2011 | Altman et al. |
| 2011/0092916 A1 | 4/2011 | Tezel et al. |
| 2011/0137286 A1 | 6/2011 | Mudd et al. |
| 2011/0150823 A1 | 6/2011 | Huang |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0213336 A1 | 9/2011 | Cucin |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner |
| 2011/0282324 A1 | 11/2011 | Kurokawa et al. |
| 2011/0282381 A1 | 11/2011 | Cronin et al. |
| 2011/0319865 A1 | 12/2011 | Buss |
| 2012/0010146 A1 | 1/2012 | Han et al. |
| 2012/0041374 A1 | 2/2012 | Lee |
| 2012/0076868 A1 | 3/2012 | Lamberti et al. |
| 2012/0089211 A1 | 4/2012 | Curtis |
| 2012/0101475 A1 | 4/2012 | Wilmot |
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0156265 A1 | 6/2012 | Binette et al. |
| 2012/0209248 A1 | 8/2012 | Gurtner et al. |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thorne |
| 2012/0296206 A1 | 11/2012 | Bahrami et al. |
| 2013/0012865 A1 | 1/2013 | Sallberg et al. |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0253289 A1 | 9/2013 | Hadvary |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310763 A1 | 11/2013 | Mudd et al. |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257179 A1 | 9/2014 | Schwab et al. |
| 2014/0257190 A1 | 9/2014 | Yue et al. |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmell |
| 2015/0025563 A1 | 1/2015 | Mosharrafa et al. |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0095984 A1 | 4/2016 | Franklin et al. |
| 2016/0114144 A1 | 4/2016 | Sumida |
| 2016/0144125 A1 | 5/2016 | Franklin |
| 2016/0207253 A9 | 7/2016 | Down et al. |
| 2016/0213854 A1 | 7/2016 | Schwab et al. |
| 2016/0263358 A1 | 9/2016 | Unger |
| 2016/0303314 A1 | 10/2016 | Momose |
| 2017/0080154 A1 | 3/2017 | Mudd et al. |
| 2017/0290987 A1 | 10/2017 | Mandaroux et al. |

FOREIGN PATENT DOCUMENTS

| | | |
|---|---|---|
| EP | 0362484 | 4/1990 |
| EP | 0205915 | 7/1990 |
| EP | 0167662 | 12/1990 |
| EP | 0648474 | 4/1995 |
| EP | 0809968 | 12/1997 |
| EP | 1051988 | 11/2000 |
| EP | 1476202 | 11/2004 |
| EP | 1486218 | 12/2004 |
| EP | 1395320 | 6/2006 |
| EP | 1859827 | 11/2007 |
| EP | 1923086 | 5/2008 |
| EP | 2189173 | 5/2010 |
| EP | 2335755 | 6/2011 |
| EP | 2422832 | 2/2012 |
| EP | 2103262 | 2/2013 |
| EP | 2184016 | 4/2013 |

(56) References Cited

FOREIGN PATENT DOCUMENTS

| | | |
|---|---|---|
| EP | 2671516 | 12/2013 |
| FR | 53011 | 9/1945 |
| FR | 2622457 | 5/1989 |
| FR | 2857654 | 1/2005 |
| GB | 2336783 | 5/2003 |
| IN | 209387 | 9/2007 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| RU | 2286803 | 11/2006 |
| WO | WO 90/001349 | 2/1990 |
| WO | WO 92/013579 | 8/1992 |
| WO | WO 94/012228 | 6/1994 |
| WO | WO 96/025965 | 8/1996 |
| WO | WO 97/028840 | 8/1997 |
| WO | WO 99/048601 | 9/1999 |
| WO | WO 01/00190 | 1/2001 |
| WO | WO 02/055135 | 7/2002 |
| WO | WO 2004/022603 | 3/2004 |
| WO | WO 2005/095225 | 10/2005 |
| WO | WO 2006/065837 | 6/2006 |
| WO | WO 2008/086479 | 8/2006 |
| WO | WO 2006/118804 | 11/2006 |
| WO | WO 2006/133111 | 12/2006 |
| WO | WO 2007/092929 | 8/2007 |
| WO | WO 2007/095922 | 8/2007 |
| WO | WO 2007/124478 | 11/2007 |
| WO | WO 2008/019265 | 2/2008 |
| WO | WO 2008/053481 | 5/2008 |
| WO | WO 2008/063569 | 5/2008 |
| WO | WO 2008/072229 | 6/2008 |
| WO | WO 2008/079824 | 7/2008 |
| WO | WO 2008/148026 | 12/2008 |
| WO | WO 2008/148071 | 12/2008 |
| WO | WO 2009/003135 | 12/2008 |
| WO | WO 2009/035680 | 3/2009 |
| WO | WO 2009/047346 | 4/2009 |
| WO | WO 2009/085548 | 7/2009 |
| WO | WO 2009/091099 | 7/2009 |
| WO | WO 2009/098666 | 8/2009 |
| WO | WO 2009/103818 | 8/2009 |
| WO | WO 2009/115581 | 9/2009 |
| WO | WO 2009/155583 | 12/2009 |
| WO | WO 2009/158145 | 12/2009 |
| WO | WO 2010/026299 | 3/2010 |
| WO | WO 2010/028025 | 3/2010 |
| WO | WO 2010/127310 | 11/2010 |
| WO | WO 2011/016785 | 2/2011 |
| WO | WO 2011/072399 | 6/2011 |
| WO | WO 2011/073796 | 6/2011 |
| WO | WO 2011/075731 | 6/2011 |
| WO | WO 2011/109129 | 9/2011 |
| WO | WO 2011/109130 | 9/2011 |
| WO | WO 2012/006587 | 1/2012 |
| WO | WO 2012/019103 | 2/2012 |
| WO | WO 2012/054301 | 4/2012 |
| WO | WO 2012/054311 | 4/2012 |
| WO | WO 2012/127856 | 9/2012 |
| WO | WO 2012/172424 | 12/2012 |
| WO | WO 2013/005881 | 1/2013 |
| WO | WO 2013/054165 | 4/2013 |
| WO | WO 2013/055832 | 4/2013 |
| WO | WO 2013/082112 | 6/2013 |
| WO | WO 2013/106857 | 8/2013 |
| WO | WO 2014/026044 | 2/2014 |
| WO | WO 2014/034032 | 3/2014 |
| WO | WO 2012/174464 | 5/2014 |
| WO | WO 2014/064536 | 5/2014 |
| WO | WO 2014/189161 | 11/2014 |
| WO | WO 2015/007243 | 1/2015 |
| WO | WO 2015/020982 | 2/2015 |
| WO | WO 2013/065235 | 4/2015 |
| WO | WO 2015/064031 | 5/2015 |
| WO | WO 2015/105269 | 7/2015 |
| WO | WO 2015/127339 | 8/2015 |
| WO | WO 2015/149031 | 10/2015 |
| WO | WO 2016/008845 | 1/2016 |
| WO | WO 2016/022865 | 2/2016 |
| WO | WO 2016/033584 | 3/2016 |
| WO | WO 2016/033586 | 3/2016 |

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968.

Galderma, "Restylane Smart Click System Injection Device," Mar. 2015, retrieved from http://www.red-dot-21.com/products/restylane-smart-click-system-injection-device-22169.

Galderma, "New Restylane Skinboosters SmartClick delivery system wins prestigious Red Dot design award," Jul. 4, 2014, retrieved from http://www.galderma.com/News/articleType/ArticleView/articleId/64/New-Restylane-Skinboosters-SmartClick-delivery-system-wins-prestigious-Red-Dot-design-award.

Hamza et al., "A new external filling device in tissue expansion," Plastic and Reconstructive Surgery, Mar. 1998, vol. 101, No. 3, pp. 813-815.

Indian Patent Application No. 190/CHE/2002, filed Mar. 20, 2002, entitled a Subcutaneous Tissue Expander.

Indian Patent Application No. IN2012KO01267 for Tissue Expander.

International Search Report from PCT/US2016/021838, dated May 17, 2016, 3 pages.

ISRWO from PCT/US2009/045831, dated Feb. 24, 2010, 14 pages.

ISRWO from PCT/US2014/039265, dated Nov. 18, 2014, 18 pages.

ISRWO from PCT/US2014/039266, dated Aug. 26, 2014, 13 pages.

Kilroy et al., "Cytokine Profile of Human Adipose-Derived Stem Cells: Expression of Angiogenic, Hematopoietic, and Pro-Inflammatory Factors," J. Cell. Physiol., 2007, 702-709.

Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.

Prime Journal, "Galderma to launch two new syringes at AMWC 2014," Mar. 2014.

Rehman et al., "Secretion of Angiogenic and Antiapoptotic Factors by Human Adipose Stromal Cells, Circulation," 2004, 1292-1298, 109.

Turtlepin, "The Painless Direct Dermal Injector" Product Information, JM Biotech Co Ltd, 2013.

Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.

Yoshimura et al., "Cell-Assisted Lipotransfer for Cosmetic Breast Augmentation: Supportive Use of Adipose-Derived Stem/Stromal Cells," Aesth. Plast. Surg., 2008, 48-55.

Yoshimura et al., "Cell-Assisted Lipotransfer for Facial Lipoatrophy: Effects of Clinical Use of Adipose-Derived Stem Cells," Dermatol. Surg., 2008, 1178-1185.

Yoshimura et al., "Characterization of Freshly Isolated and Cultured Cells Derived From the Fatty and Fluid Portions of Liposuction Aspirates," J Cell Physiol, 2006, 1011-1041.

\* cited by examiner

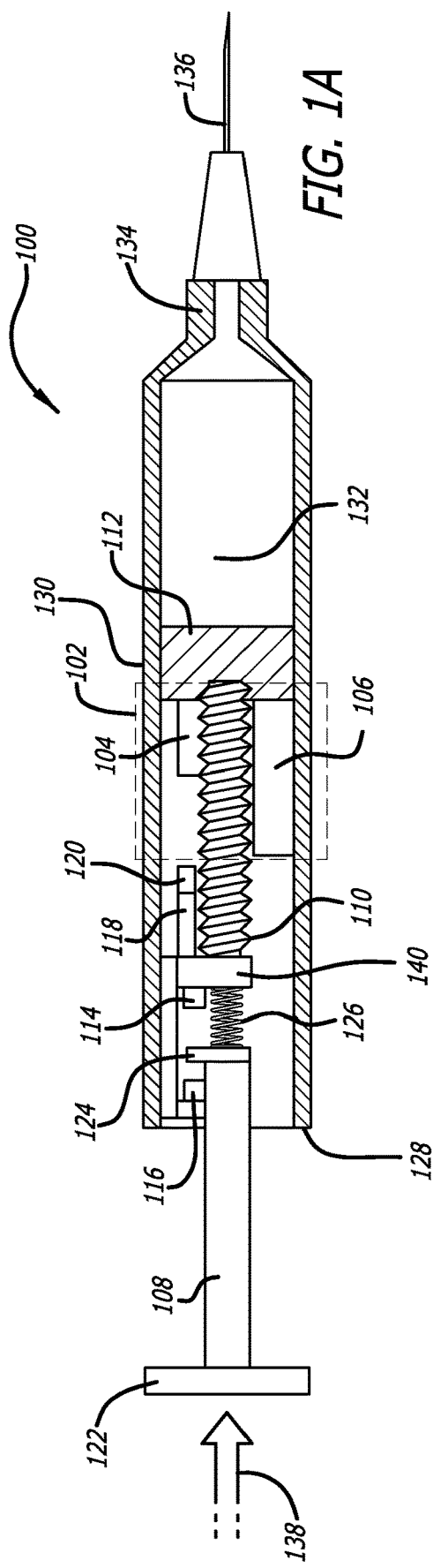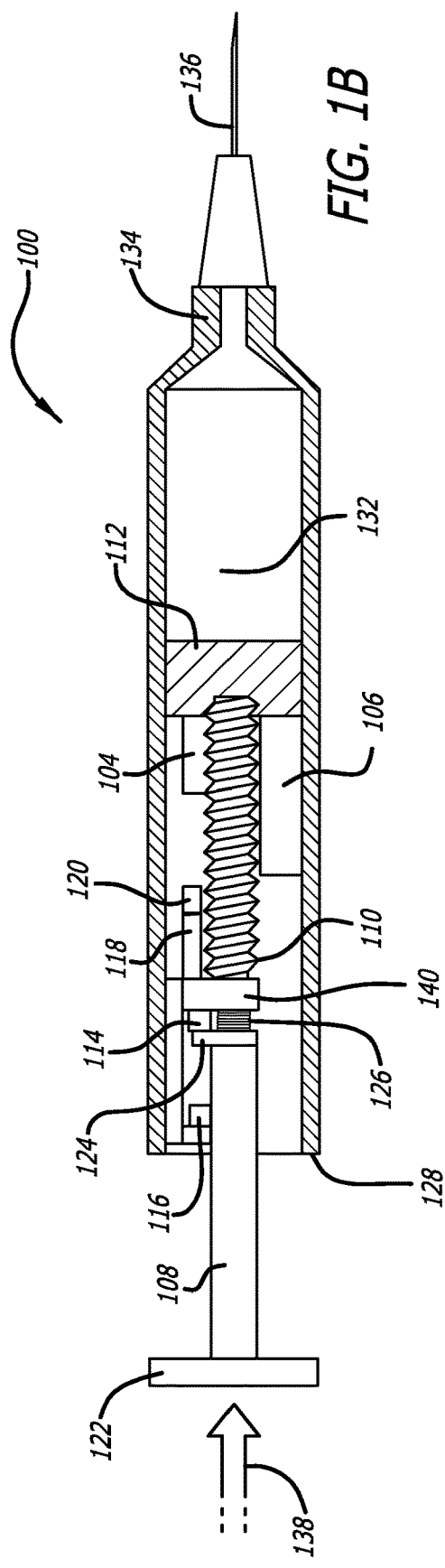

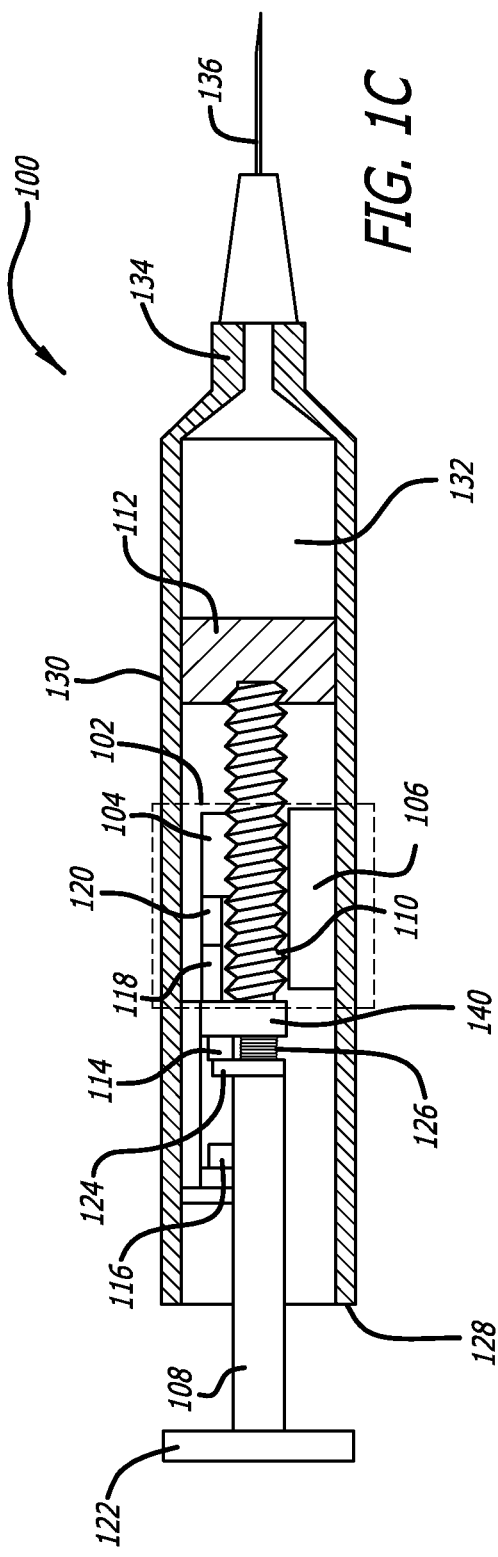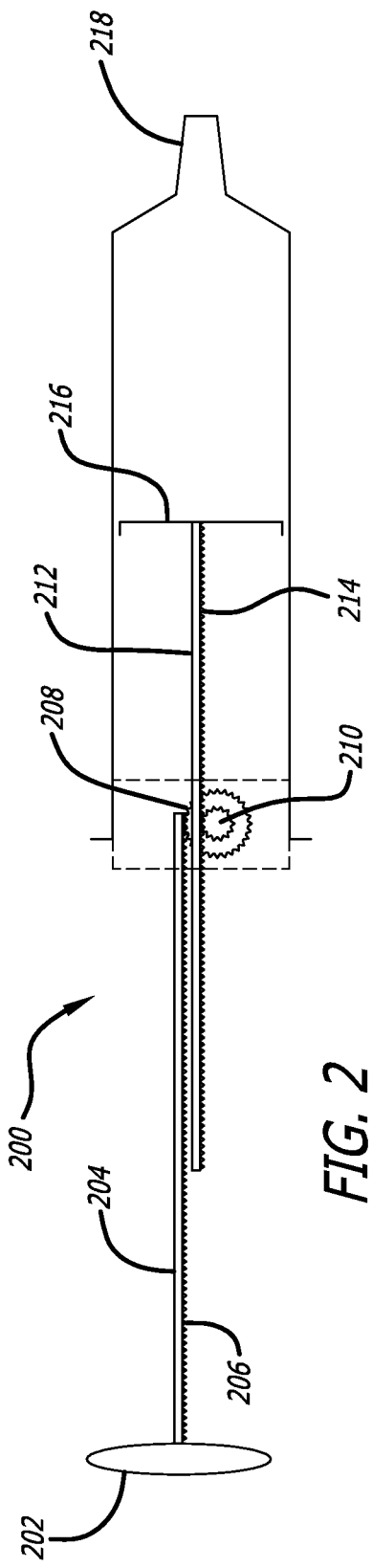

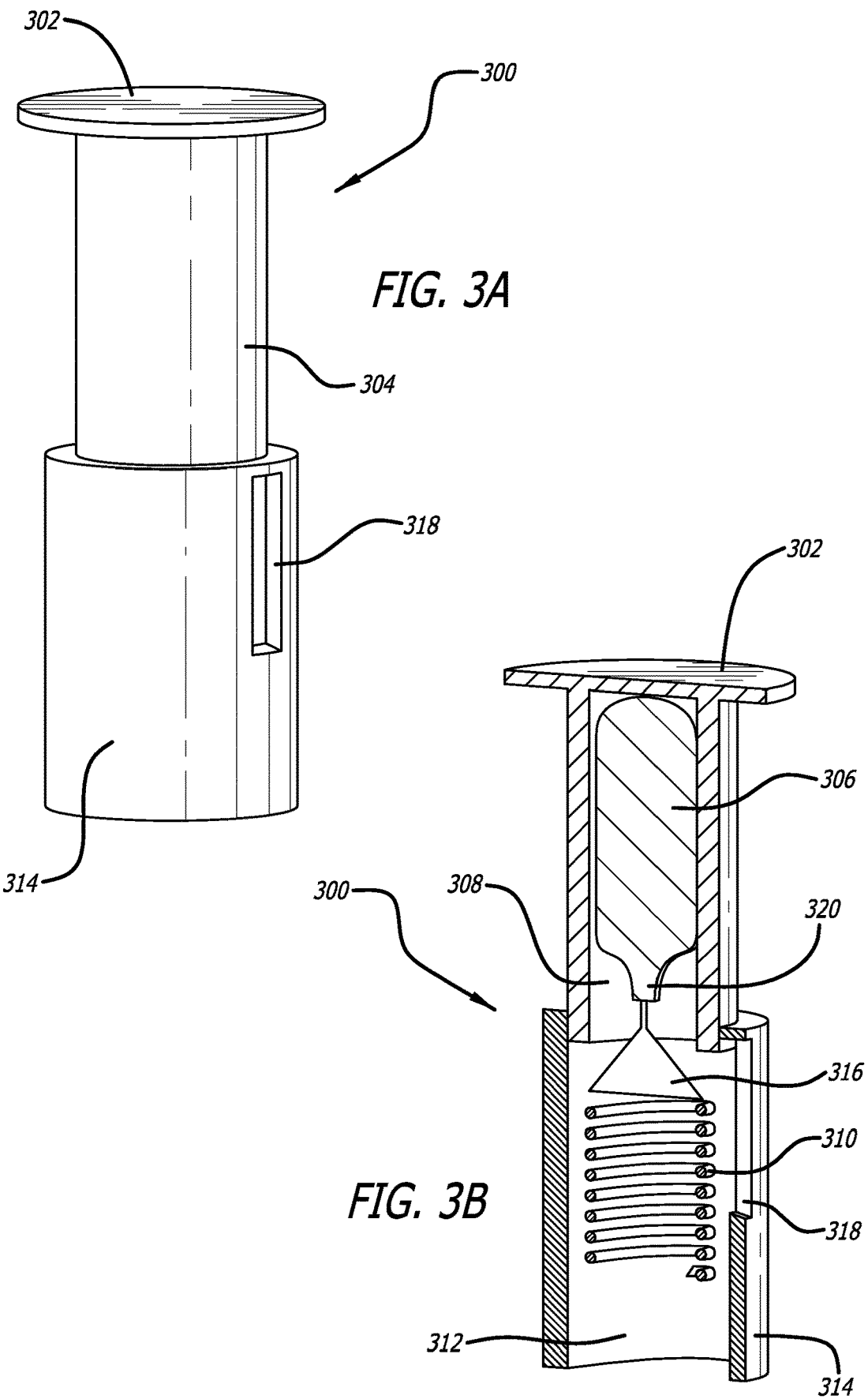

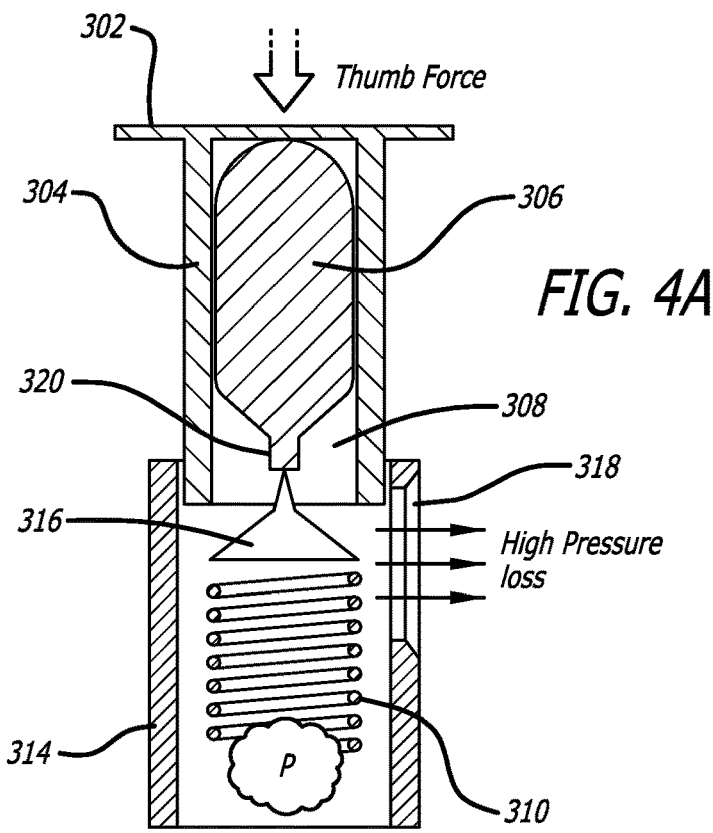
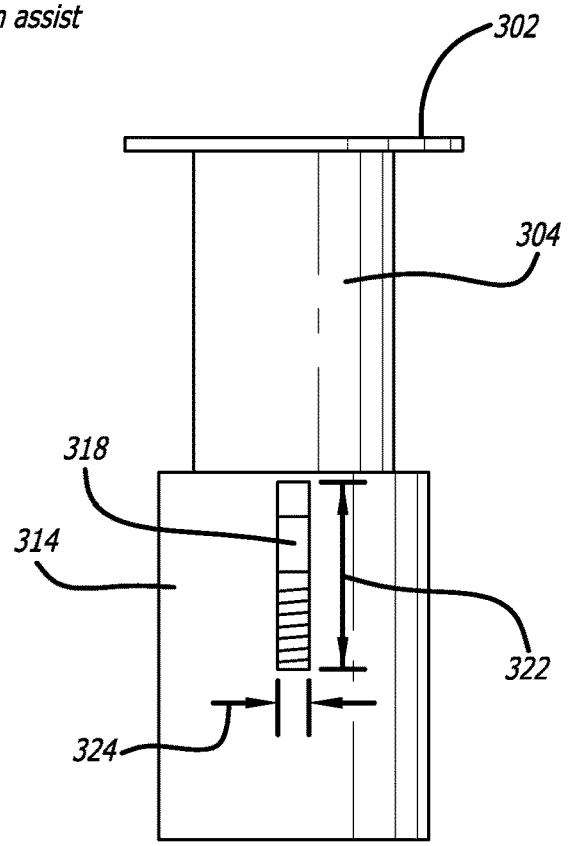
FIG. 4A
FIG. 4B

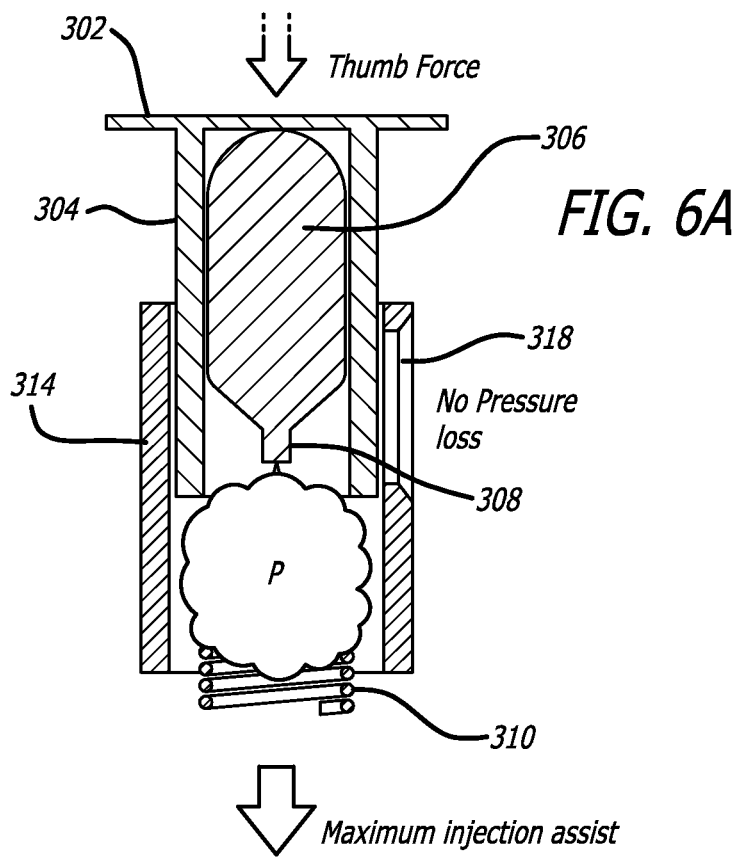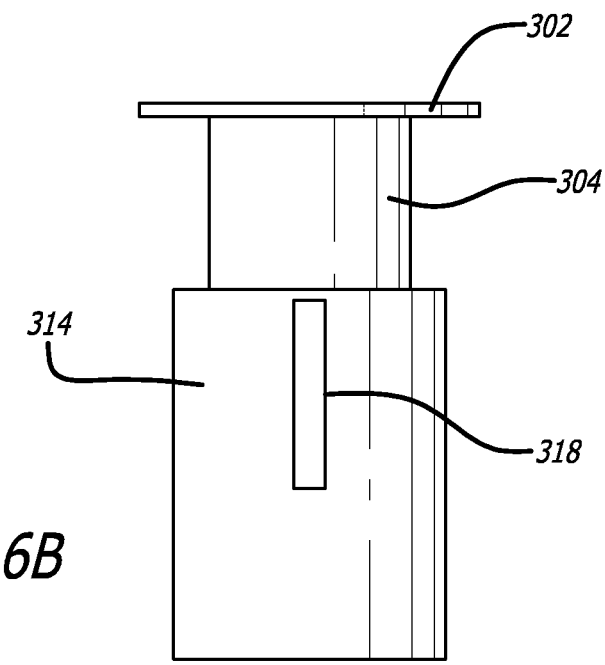

HIGH FORCE INJECTION DEVICES

CROSS-REFERENCE TO RELATED APPLICATIONS

This application is a continuation application of U.S. application Ser. No. 14/702,581, filed on May 1, 2015, which claims the benefit of U.S. Provisional Application No. 61/992,380, filed on May 13, 2014, the entirety of each of which is incorporated herein by reference.

FIELD

The present invention generally relates to medical injection devices, and more specifically relates to injection devices used to extrude highly viscous materials.

BACKGROUND

Injection of liquids, gels, and gases through a syringe is common practice in many applications including both medical and nonmedical purposes. When injecting highly viscous materials requiring high force and/or pressure using a standard syringe, users may experience a high injection force for extrusion and/or aspiration. Some medical examples of high force applications are Fat Grafting and Facial Fillers.

Many of these injectable materials, for example, dermal fillers and fat grafting materials, are not easily extruded through standard syringes and accompanying cannula. These materials tend to provide significant resistance to be pushed through a narrow cannula. The problem is even more exacerbated by the fact that these materials are often used for detailed precision work in facial contouring and body sculpting.

A need exists for devices that can be attached to or used in place of a standard syringe and which provide better control over dosing of relatively difficult to inject materials, for example, dermal fillers, fat grafting materials and the like.

SUMMARY

Devices and methods, in particular syringes, are described herein that can provide assistance with extruding and/or aspirating high viscosity materials such as, but not limited to, gels or fluids. These viscous materials can be, for example, but not limited to, a dermal filler, a fat grafting material, an epoxy, caulking, or a combination thereof. The devices can be a variation of a standard syringe and can include electromechanical or mechanical assistance with injection or extrusion.

Described herein are electromechanical assisted syringes. These syringes can include: at least one motor configured to drive a plunger tip; a plunger configured to activate the motor; and a spring configured to provide a spring force. Further, these syringes allow a user to apply a force to the plunger which can overcome the spring force. This force is then translated by the motor into a higher force to extrude a viscous material from the electromechanical assisted syringe.

The electromechanical assisted syringes can further include a lead screw operably coupling the motor to the plunger tip. The electromechanical assisted syringes can further include a carriage including a printed circuit board, wherein the carriage is configured to move with the lead screw. The carriage can be attached to a distal end of the lead screw.

The plunger can include a selector end configured to engage a forward button when the spring force has been overcome. Here, the forward button can be configured to activate the motor to drive the lead screw clockwise. The selector end of the plunger can also be configured to engage a reverse button when the spring force has been overcome. Here, the reverse button can be configured to activate the motor to drive the lead screw counterclockwise.

Methods of using these electromechanical assisted syringes are also described herein.

Also described herein are compressed air assisted syringes. These compressed air assisted syringes can include: a plunger configured to receive an extrusion force and house at least one compressed air cartridge; a spring configured to hold a piercing element; and a compression chamber.

In some embodiments, these compressed air assisted syringes are provided such that when a force is applied to the plunger, the at least one compressed air cartridge engages the piercing element thereby releasing compressed air into the compression chamber. The compressed air in the compression chamber can push on a plunger tip to extrude at least one material from the compressed air assisted syringe.

Compressed air assisted syringes can include at least one pressure bleed orifice in the compression chamber. The compressed air assisted syringes can be configured such that when the bleed orifice is fully open a minimal extrusion assistance is provided to the plunger tip. Likewise, the compressed air assisted syringes can be configured such that when the bleed orifice is fully closed a maximum extrusion assistance is provided to the plunger tip.

The bleed orifice can be configured to be opened and closed. The compressed air assisted syringes can be configured such that when the bleed orifice is more open the compressed air assisted syringe can be configured to provide less assistance to the plunger tip. Likewise, the compressed air assisted syringes can be configured such that when the bleed orifice is more closed the compressed air assisted syringe can be configured to provide more assistance to the plunger tip.

Methods of using these compressed air assisted syringes are also described herein.

Methods of assisting an injection of a viscous material are also provided using the assisted syringes described herein. In some embodiments, the methods include: applying an extrusion force to a plunger of an assisted syringe thereby extruding the viscous material from the assisted syringe with a higher force than the extrusion force. In some embodiments, the assisted syringes include at least one motor, at least one compressed air cartridge, or a combination thereof which is configured to provide the higher force to a plunger tip.

BRIEF DESCRIPTION OF THE DRAWINGS

Embodiments of the present description are illustrated by way of example, and not by way of limitation, in the figures of the accompanying drawings and in which like reference numerals refer to similar elements, wherein:

FIG. 1A illustrates an example electromechanical syringe as described herein. FIG. 1B illustrates the electromechanical syringe of FIG. 1A with force applied to the plunger head. FIG. 1C illustrates the electromechanical syringe of FIG. 1A with force applied to the plunger head for a period of time so that the plunger tip has moved thereby injecting or extruding a material.

FIG. 2 illustrates an example mechanical assistance syringe.

FIG. 3A illustrates an external view of an assistance portion of a syringe that uses pressurized air. FIG. 3B is a cross-section of the portion illustrated in FIG. 3A.

FIG. 4A is a cross-section of the portion illustrated in FIG. 3A with minimal force applied to the plunger head. FIG. 4B illustrates an external view of an assistance portion of FIG. 4A.

FIG. 6A is a cross-section of the portion illustrated in FIG. 3A with maximum force applied to the plunger head. FIG. 6B illustrates an external view of an assistance portion of FIG. 6A.

DETAILED DESCRIPTION

Figure 5A:
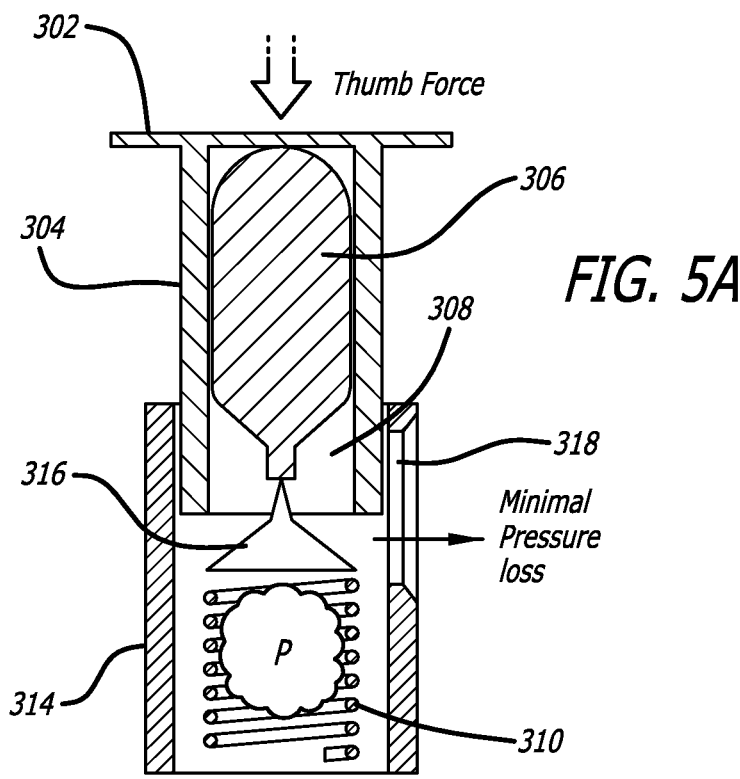
FIG. 5A is a cross-section of the portion illustrated in FIG. 3A with moderate force applied to the plunger head.

Generally described herein are devices and methods for extruding and/or aspirating high viscosity materials. In some embodiments, these high viscosity materials can be gels or fluids. The devices can be a variation of a standard syringe including mechanical or electro-mechanical elements, while keeping a familiar, syringe-style user interface. The embodiments can be applied to either re-usable or single use applications. In some embodiments, the syringes described can be completely independent from a standard syringe.

The syringes described herein can be assisted syringes. The assisted syringes described herein can achieve at least one of: relieving the user from high injection/aspiration forces associated with highly viscous gels/fluids and/or high gauge needles; having little impact on the user's preferred style of injection; and keeping extrusion/aspiration speed to a controlled level. The assisted syringes can provide assistance via one or more motors, one or more compressed gasses, or a combination thereof.

The syringes described herein can provide a high force to extrude a viscous material. This high force can be based on a lesser extrusion force applied to the syringe's plunger. The high force can be greater than about 1 Newton (N), greater than about 2 N, greater than about 3 N, greater than about 4 N, greater than about 5 N, greater than about 10 N, greater than about 20 N, greater than about 40 N, greater than about 60 N, greater than about 80 N, greater than about 100 N, between about 1 N and about 20 N, between about 1 N and about 100 N, or between about 20 N and about 100 N.

In general, the syringes described herein can have variations of components found in standard syringes such as, but not limited to a plunger, a plunger tip, an internal volume to hold a material to be injected, and a luer tip or other connection device or a needle or cannula permanently attached.

In some embodiments, the devices can further include electromechanics for pressure relief and/or adding force and/or a unit to control and sense forward and reverse functions of the devices.

Some example devices can be motorized. In a motorized embodiment, as illustrated in FIGS. 1A-B, an electro-mechanical syringe 100 can be provided to reduce injection force by utilizing a transmission 102. The transmission can include at least one gear 104 and at least one motor 106. The transmission can be controlled by a suspended plunger 108, and may interact with a lead screw 110 that pushes/pulls plunger tip 112, causing extrusion or aspiration.

In some embodiments, transmission 102 is stationary, while lead screw 110 is meant to travel as a result of being driven by gears 104. Lead screw 110 can be configured to simulate the user's manual injection.

In some embodiments, "electronics" as used herein can include, but is not limited to at least one motor(s) 106, forward button 114, reverse button 116, battery 118, and a printed circuit board 120 which includes at least one processor and memory. The electronics can control speed of a plunger at least to some degree.

Electro-mechanical syringe 100 further includes a plunger force application surface 122 at proximal end of plunger 108 and a selector end 124 at distal end of plunger 108. Selector end 124 is operatively attached to spring 126 that can be compressed when a force is applied to plunger force application surface 122. When compressed with enough force, selector end 124 can depress forward button 114 thereby relaying a signal to the printed circuit board 120 which in turn engages motor 106 to drive lead screw 110 forward.

When lead screw 110 is driven forward, plunger tip 112 drives through material cavity 132 and extrudes material housed therein through coupling section 134 and out needle 136.

Likewise, selector end 124 can be expanded when plunger 108 is pulled away from proximal end 128 of syringe body 130. When force application surface 122 is pulled, spring 126 can be expanded and selector end 124 can depress reverse button 116 thereby relaying a signal to the printed circuit board 120 which in turn engages motor 106 to drive lead screw 110 in reverse or toward proximal end 128.

When lead screw 110 is driven in reverse, plunger tip 112 is driven backward thereby increasing the volume of material cavity 132 thereby aspirating material or air into material cavity 132.

When spring 126 is a rest, such as when no forces are being applied to plunger 108, selector end 124 does not depress either forward button 114 or reverse button 116. In such an embodiment, spring 126 can be at rest.

FIG. 1B illustrates that when a user applies enough force 138 on plunger force application surface 122, spring 126 is compressed and selector end 124 advances toward forward button 114. When forward button 114 is pressed, motor 106 is activated.

FIG. 1C illustrates that after motor 106 has advanced lead screw 110, the plunger tip 112 and all internal components except motor 106 and gears 104 or transmission 102 have been displaced as a single unit in unison to simulate a manual injection, and extrusion has occurred. Everything except the transmission can include plunger 108, spring 126, printed circuit board 120, battery 118, forward button 114, reverse button 116, lead screw 110 and plunger tip 112.

In some embodiments, printed circuit board 120, battery 118, forward button 114, and reverse button 116 can all be attached to a carriage 140. Carriage 140 can be attached to the proximal end of lead screw 110.

Motor 106 as described herein can be any motor with enough output power to turn lead screw 110, advance plunger tip 112 and extrude the contents of material cavity 132. Motor 106 can be one or more motor or actuators to move lead screw 110. The motor(s) and/or actuator(s) can drive one or more gears 104 and can be driven by an appropriate voltage ultimately provided by battery 118. Motor 106 can have a maximum stall torque of 7,500 g cm, 5,000 g cm, or 4,480 g cm. The stall torque can have a minimum of 100 g cm, 250 g cm, or 396 g cm. The maximum efficiency torque can have a maximum of 1,500 g cm, 1,000 g cm, or 900 g cm. The maximum efficiency torque can have a minimum of 50 g, 75 g cm, or 88 g cm. Further, the gear ratio of the motor and/or actuator can have a maximum of about 500:1, 350:1, or 300:1. The gear ratio of the motor and/or actuator can have a minimum of about 10:1, 25:1, 30:1, or 100:1. In one embodiment, the gear ratio can be about 298:1. In one embodiment, the motor is a Firgelli GM12-N20VA-08260-298-R gearmotor (Firgelli Technologies, Inc. Victoria, BC, Canada).

In some embodiments, as an alternative to a motor, a solenoid can be used. The solenoid can be used for gearing to control the speed and reduce injection force. A latching or continuous solenoid can act as a ratchet for a gear mechanism (such as that illustrated in FIG. 2) and may be powered by an internal energy source such as a battery.

One skilled in the art will appreciate that there are several gear/motor combinations which can be used to achieve various linear drive speeds of lead screw 110 and ultimately plunger tip 112. In one embodiment, electro-mechanical syringe 100 may comprise one or more worm gears.

Printed circuit board 120 can be configured to control electronic functions of the syringe. Printed circuit board 120 can control motor 106 and other powered components. Printed circuit board 120 can be used to regulate the current and/or voltage delivered to the various electronic parts such as motor 106. By adjusting the current and/or voltage of motor 106, for example, the speed and force applied for material extrusion and/or aspiration can be regulated.

The electro-mechanical syringes described herein can be powered by one or more batteries, such as battery 118. Batteries may be common non-rechargeable types such as, but not limited to, A, AA, AAA, C, D, and 9V. The one or more batteries used may be rechargeable batteries. The rechargeable battery(s) can be charged through induction or through direct-connect interface to an AC/DC power source. In one embodiment, the rechargeable battery(s) may be a permanent battery that charges within the devices and is not removed by the operator. The rechargeable battery(s) may be semi-permanent meaning they are charged inside the devices, but can be replaced if the battery(s) expires or malfunctions over time. The rechargeable battery(s) may be operator replaceable of either standard or non-standard type batteries. The operator replaceable rechargeable batteries may be charged within the devices or outside the devices. The operator replaceable rechargeable batteries charged outside the devices can be specific for the devices and comprise a series of standby batteries ready for rapid swapping.

The electro-mechanical syringes can include one or more means of storage associated with printed circuit board 120. The storage can be built-in internal storage (e.g. random access memory, flash memory, read only memory, microdrive). The internal storage may be built directly into printed circuit board 120. The storage can be an external source. The device can comprise a slot to which an external storage device may be connected or inserted. Such external storage devices include, but are not limited to universal serial bus (USB) drives, firewire drives, flash and media cards, and microdrives.

The internal or external storage can contain information about electro-mechanical syringe 100 and/or a cartridge or product being injected from material cavity 132. The information can include, but is not limited to, operating software, firmware, device usage statistics, patient information, patient name, patient identification, material name, material part number, material Rx number, material lot number, material expiration date, date of injection(s), time of injection(s), area(s) of injection(s), injection volume(s), injection volume(s) per area injected, total volume injected, and operator name.

Any and all information provided from the storage or processed by printed circuit board 120 can be provided on a display associated with syringe body 130. The display may be curved in order to conveniently associate with the body without providing manipulation obstacles. One or more buttons can be located on syringe body 130 to control functions processed by printed circuit board 120.

The syringes may have the ability to drive motor 106 at variable speeds to facilitate different rates of extrusion of material. The syringes may have sensors operably associated with printed circuit board 120 to quantify the velocity of lead screw 110 and verify the desired extrusion rate. The sensors may provide feedback to printed circuit board 120 allowing it to drive motor 106 faster or slower if the desired extrusion rate is not being met.

Electro-mechanical syringe 100 can inject highly viscous materials through a various range of needle gauges. Needle 136 can have a gauge as high as 50, more generally in the range of about 10 to about 33, generally about 30. The devices can extrude material at a rate of about 0.001 to about 1 mL/sec. Other extrusion speeds can be between 0.004 to 0.05 mL/sec. The rate of extrusion may be dependent of the viscosity of the material being extruded and the density of the tissue or material being injected. A highly viscous material will require much more extrusion force than will a low viscosity material. The syringes described herein can generate extrusion forces up to 100 N. The syringes preferably provide forces of 20 to 100 N, more preferably about 20 to 90 N. The extrusion force should not exceed a safe range for a patient. A person skilled in the art can easily determine the rate of injection relative to the viscosity of the material and density of the tissue or material being injected. The syringes can have adjustable extrusion force to match the desired extrusion rate of the material.

In some embodiments, the materials to be extruded may be non-Newtonian or mixtures of Newtonian and non-Newtonian fluids. Such fluids can have inconsistent and/or unpredictable force-to move requirements. Such products can have high yield points requiring high stall torque requirements. Non-Newtonian fluids may have high yield points but have rapid drops in force-to-move requirements after the yield point is overcome. As such, the syringes described herein can accommodate for rapid changes in extrusion force requirements.

In one embodiment, the syringes can achieve a steady state of material extrusion despite changes in fluid consistency and/or viscosity, including differing yield points. Additionally, in some embodiments, two or more different materials can be utilized requiring enough force to overcome two or more different yield points at two or more different times during extrusion. As such, the syringes can be equipped with electronics on printed circuit board 120 that can constantly monitor the delivery force, speed, and pressure to name a few.

In one embodiment, a motorized injection device as described herein can be re-usable. A reusable motorized device can require a mechanism to insert/detect disposable cartridges and a battery charging feature or at least a replaceable battery. In one embodiment, at least one cartridge can be housed in syringe body 130 in place of material cavity 132. Such a cartridge may be ejected manually, automatically, or semi-automatically. Automatic methods can be devised using one or more of the following, non-limiting components: motor (e.g. gear or stepper), gears (e.g.

rack and pinion, worm or worm gear), linear actuator, air piston, springs (e.g. compression or extension) and/or magnets.

The electro-mechanical syringes described herein may contain a force or strain gauge used to measure the puncture force and depth of needle 136 through a patient's skin. The depth of the injection can be important for certain types of materials and their respective absorption rates. The puncture force can be instrumental to reducing injection pain as it can serve to adjust the force of the needle puncture depending on the skin type and needle gauge.

In one embodiment, the electro-mechanical syringes described herein can include a linear variable differential transformer (LVDT). An LVDT can be used to measure liner displacement. The LVDT can be used to measure the depth of needle 136 through the patient's skin or tissue or can be used to measure the depth of plunger tip 112 into material cavity 132, thereby measuring the amount of material extruded from or aspirated into the syringe.

The electro-mechanical syringes described herein may further include a temperature controlled unit. The unit can comprise a jacket that surrounds material cavity 132 thereby allowing the user to keep housed materials either heated or cooled before, during, and between injections. This may be more critical for some materials more than others. For example, materials that must be kept refrigerated would benefit from this technology.

The electromechanical syringes described herein can translate standard injection force for a material such as saline into a plunger tip force that can extrude a highly viscous material without detection by the user.

In some embodiments, a simple set of forward and reverse buttons can be replaced by a variable slider. This variable slider can allow for dynamic injection speeds, and not just a binary switch based operation. A variable slider can ramp up the extrusion speed depending on the amount of force applied to the plunger. Likewise, a variable slider can ramp up the aspiration speed depending on the amount of backward force applied to the plunger.

In some embodiments, electromechanical syringes described herein can inject more than one material. In some embodiments, the materials are mixed using a static or dynamic mixing mechanism as the materials are extruded. In some embodiments, one set of motor, gear and lead screw can be used to drive two different plunger tips simultaneously. In other embodiments, two different motors, gears, and lead screws can be used to extrude two materials at independent rates. Two independent systems can be used when different extrusion forces are required for each material.

In some embodiments, two, three, four, five, six or more materials can be mixed and/or extruded together. In one embodiment, the electromechanical syringes described herein can be used to extrude various epoxy/glue combinations that require mixing while extruding.

In another embodiment, syringes may not include a motor and require a mechanical mechanism to reduce the force required to extrude high viscosity materials. Such a mechanism can include a gear system that reduces injection or extrusion force, but may increase plunger travel length. A gear reduction translates into a decrease in injection force, but an increase in plunger travel length.

The syringes in one embodiment can include: at least one motor configured to drive a plunger tip; a plunger configured to activate the motor; and a spring configured to provide a spring force. Further, these syringes can allow a user to apply a force to the plunger which can overcome the spring force. This force is then translated by the motor into a higher force to extrude a viscous material from the electromechanical assisted syringe.

The plunger can include a selector end configured to engage a forward button when the spring force has been overcome thereby fully compressing the spring, and the forward button can be configured to activate the motor to drive the lead screw clockwise. The selector end of the plunger can also be configured to engage a reverse button when the spring force has been overcome and the spring has been extended, and the reverse button can be configured to activate the motor to drive the lead screw counterclockwise.

For example as illustrated in FIG. 2, mechanism 200 works by applying a force to plunger head 202 which drives plunger stem 204. Tracks 206 on plunger stem 204 can spin larger first gear 208 in a clockwise direction. A second smaller gear 210 can be operatively attached to larger first gear 208 and also spin in a clockwise direction. Second smaller gear 210 can then drive a plunger tip stem 212 via tracks 214. Plunger tip stem 212 can in turn drive plunger tip 216 thereby extruding material from tip 218. Mechanism 200 can translate a longer plunger travel length into a shorter plunger travel length and thereby reduce the amount of force required to move plunger tip.

In other mechanical embodiments, a pulley system can be used to decrease injection force, but increase plunger travel length. In such an embodiment, two, three, four five, six or more pulleys can be used to decrease input force while increasing plunger travel length.

In another mechanical embodiment, compressed air can be used to support high force injection applications. In one embodiment, pressurized air is used to assist a user when extruding or injecting by combining the force applied by a finger such as a thumb and a controlled release of compressed air via a cartridge.

In some embodiments, the compressed air can be any non-toxic or non-dangerous compressed gas. Example gases can include, but are not limited to, carbon dioxide, air, argon, nitrogen, helium, and the like, and combinations thereof. Combinations of gasses can also be used.

The cartridge can be disposable or reusable. In some embodiments, the cartridges can be disposable after a single use.

A mechanical syringe that utilizes assistance by a compressed gas may replace the use of a standard syringe. The assistance portion of such a syringe is illustrated in FIGS. 3A-B, 4A-B, 5A-B, and 6A-B. Compressed gas assistance syringe can include assistance portion 300. As illustrated in FIGS. 3A-B, assistance portion 300 includes a plunger head 302 to apply an injection or extrusion force, a plunger stem 304, a compressed gas cartridge 306 housed in cartridge chamber 308 within plunger stem 304, a spring 310 operably attached within compression chamber 312 inside syringe body 314 and configured to hold piercing element 316, and pressure bleed orifice 318. Compression chamber 312 resides directly above and in pressurized contact with a plunger tip (not illustrated).

To use assistance portion 300, as illustrated in FIGS. 4A-B, when ready to inject, a user depresses or applies force to plunger head 302 moving compressed gas cartridge tip 320 toward piercing element 316. With enough force applied to plunger head 302, compressed gas cartridge tip 320 can be pierced by piercing element 316 when spring 310 is compressed enough to disallow further movement of piercing element 316. As compressed gas is bleed into compression chamber 312, it becomes pressurized thereby applying a force to a plunger head. With pressure applied to the plunger head, material can be extruded from the syringe.

Pressure bleed orifice 318 can be located anywhere on syringe body 314. In one embodiment, it can be located on the side of syringe body 314 as illustrated. This placement of bleed orifice 318 can effectively allow a user to control with depression of their thumb on plunger head 302, how much pressurized assistance they may require. Minimal depression of plunger head 302, as illustrated in FIGS. 4A-B allows much of the pressurized air to escape through bleed orifice 318, providing minimal assistance and benefit to the user. However, full depression of plunger head 302, as illustrated in FIGS. 6A-B, can provide the user with maximum pressurized assistance, helping with difficult or high force extrusions or injections.

Varying amounts of force applied to plunger head 302 can provide varying amounts of pressurized assistance. For example, as illustrated in FIGS. 5A-B, a moderate force applied to plunger head 302 can provide a moderate assistance.

The vertical nature of bleed orifice 318 provides this variability of assistance. Bleed orifice 318 can have a generally vertical rectilinear shape. For example, vertical opening length 322 is longer than horizontal opening length 324.

The percentage of opening of bleed orifice 318 can be inversely proportional to the amount of assistance. For example, as illustrated in FIG. 4B when minimal force is applied to plunger head 302, about 80% of bleed orifice is open to allow compressed air to bleed out of compression chamber 312. This translates to about 20% assistance to extrusion or injection.

Figure 5B:
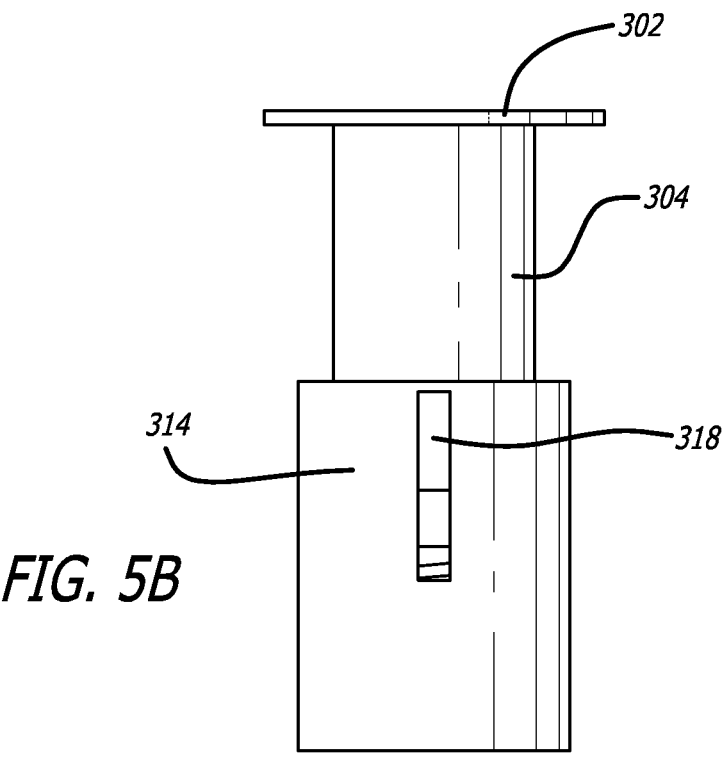
FIG. 5B illustrates an external view of an assistance portion of FIG. 5A.

Likewise, as illustrated in FIG. 5B when moderate force is applied to plunger head 302, about 50% of bleed orifice is open to allow compressed air to bleed out of compression chamber 312. This translates to about 50% assistance to extrusion or injection.

When about 20% of bleed orifice is open to allow compressed air to bleed out of compression chamber 312. This translates to about 80% assistance to extrusion or injection.

As illustrated in FIG. 6B when maximal force is applied to plunger head 302, about 100% of bleed orifice is closed thereby preventing compressed air from bleeding out of compression chamber 312. This translates to 100% assistance to extrusion or injection.

Generally, about 5% opening in bleed orifice 318 translates to about 95% assistance, about 10% opening in bleed orifice 318 translates to about 90% assistance, about 20% opening in bleed orifice 318 translates to about 80% assistance, about 30% opening in bleed orifice 318 translates to about 70% assistance, about 40% opening in bleed orifice 318 translates to about 60% assistance, about 50% opening in bleed orifice 318 translates to about 50% assistance, about 60% opening in bleed orifice 318 translates to about 40% assistance, about 70% opening in bleed orifice 318 translates to about 30% assistance, about 80% opening in bleed orifice 318 translates to about 20% assistance, about 90% opening in bleed orifice 318 translates to about 10% assistance, and about 95% opening in bleed orifice 318 translates to about 5% assistance. These ranges can be modified by changing the general shape or configuration of bleed orifice 318.

In another embodiment, pressure assistance can be altered by reversing bleed orifice 318. In this embodiment, all of the pressure generated from the initial compressed gas cartridge puncture can be stored in the syringe thereby providing the most injection or extrusion assistance. This initial storage of compressed gas can be possible because the bleed orifice is located at a lower position thereby requiring more force to allow pressure to bleed. As plunger head 302 is depressed with the thumb, the user can control the amount of pressure leak that leaks by gradually opening the window. This may allow for more compact designs due to the prevention of pressure loss at the time of initial injection.

The above assistance portion 300 illustrates plunger head 302 can act as a spring-action button, and is stationary with respect to the plunger/fluid element. In another embodiment, plunger head 302 can travel with the plunger tip to simulate a more syringe-like motion during injection (as in previous embodiments). In other words, in a more syringe injection like mechanism, the pressurized assistance moves axially through the syringe body as material is extruded.

In one embodiment, the compressed air syringes can include: a plunger configured to receive an extrusion force and house at least one compressed air cartridge; a spring configured to hold a piercing element; and a compression chamber.

The compressed air syringes can be provided such that when a force is applied to the plunger, the at least one compressed air cartridge engages the piercing element thereby releasing compressed air into the compression chamber. The compressed air in the compression chamber can then push on a plunger tip to extrude at least one material from the compressed air assisted syringe.

Compressed air assisted syringes can include at least one pressure bleed orifice in the compression chamber. The compressed air assisted syringes can be configured such that when the bleed orifice is fully open a minimal extrusion assistance is provided to the plunger tip. Likewise, the compressed air assisted syringes can be configured such when the bleed orifice is fully closed a maximum extrusion assistance is provided to the plunger tip.

As described herein, the bleed orifice can be configured to be opened and closed using the plunger stem to close the orifice. The compressed air assisted syringes can be configured such that when the bleed orifice is more open the compressed air assisted syringe can be configured to provide less assistance to the plunger tip. Likewise, the compressed air assisted syringes can be configured such that when the bleed orifice is more closed the compressed air assisted syringe can be configured to provide more assistance to the plunger tip.

The assistance devices described herein can be relatively simple to use, with a minimal learning curve. The user can fill their syringe using any standard means or can use an assisted method or device as described. Then, injection can be made easier via the assistance provided by the devices described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible.

Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A compressed gas assisted syringe comprising:
    a syringe body comprising a material cavity, a compression chamber, and a pressure bleed orifice;
    a plunger head disposed proximal to the syringe body and configured to receive an applied force;
    a plunger stem extending distally from the plunger head into the syringe body, the plunger stem comprising a cartridge chamber configured to house a compressed gas cartridge; and
    a piercing element disposed in the syringe body and configured to engage the compressed gas cartridge in response to the applied force,
    wherein the piercing element is configured to release a compressed gas into the compression chamber to push on the plunger head to provide extrusion assistance, the pressure bleed orifice is configured to allow the released compressed gas to bleed from the compression chamber, and an opening percentage of the pressure bleed orifice is adjustable to provide an inversely proportional amount of the extrusion assistance.

2. The compressed gas assisted syringe of claim 1, further comprising:
    a spring disposed in the compression chamber and configured to hold the piercing element against the compressed gas cartridge.

3. The compressed gas assisted syringe of claim 1, wherein a first opening percentage of the pressure bleed orifice is configured to provide a first amount of the extrusion assistance by allowing the released compressed gas to bleed from the compression chamber at a first rate, and wherein a second opening percentage of the pressure bleed orifice greater than the first opening percentage is configured to provide a second amount of the extrusion assistance less than the first amount by allowing the released compressed gas to bleed from the compression chamber at a second rate greater than the first rate.

4. The compressed gas assisted syringe of claim 1, wherein the pressure bleed orifice is disposed on a lateral side of the syringe body.

5. The compressed gas assisted syringe of claim 4, wherein the plunger stem is configured to at least partially block an opening of the pressure bleed orifice, and wherein axial movement of the plunger stem relative to the syringe body is configured to change an amount by which the plunger stem partially blocks the opening to change an amount of the extrusion assistance.

6. The compressed gas assisted syringe of claim 1, wherein the syringe body is elongated in a longitudinal direction, wherein the pressure bleed orifice is longer in the longitudinal direction than in a circumferential direction relative to the syringe body.

7. The compressed gas assisted syringe of claim 6, wherein the pressure bleed orifice has a generally rectilinear shape extending in the longitudinal direction.

8. A method of extrusion from a compressed gas assisted syringe, the method comprising:
    applying a force to a plunger head disposed proximal to a syringe body, the syringe body comprising a material cavity and a compression chamber, the material cavity housing a material therein;

moving a plunger stem distally into the syringe body, the plunger stem comprising a cartridge chamber housing a compressed gas cartridge;

moving the plunger head to extrude the material housed therein;

releasing a compressed gas from the compressed gas cartridge into the compression chamber;

bleeding at least a portion of the released compressed gas through a pressure bleed orifice disposed in the syringe body;

adjusting an opening of the pressure bleed orifice to provide an inversely proportional amount of extrusion assistance; and pushing on the plunger head with the released compressed gas to provide the extrusion assistance.

9. The method of claim 8, further comprising:

compressing a spring disposed in the compression chamber, the spring holding a piercing element against the compressed gas cartridge, wherein the compressed gas is released by piercing the compressed gas cartridge with the piercing element.

10. The method of claim 8, further comprising: (i) increasing an opening of the pressure bleed orifice to reduce an amount of the extrusion assistance, or (ii) decreasing an opening of the pressure bleed orifice to increase an amount of the extrusion assistance.

11. The method of claim 10, wherein: (i) the opening is increased by moving the plunger stem in a first direction to block the opening with the plunger stem by a first amount, or (ii) the opening is decreased by moving the plunger stem in a second direction opposite to the first direction to block the opening with the plunger stem by a second amount greater than the first amount.

12. A compressed gas assisted syringe comprising:

a syringe body comprising a material cavity, a compression chamber, and a pressure bleed orifice;

a plunger head disposed proximal to the syringe body and configured to receive an applied force;

a plunger stem extending distally from the plunger head into the syringe body, the plunger stem comprising a cartridge chamber configured to house a compressed gas cartridge, wherein the plunger stem is configured to at least partially block an opening of the pressure bleed orifice; and a piercing element disposed in the syringe body and configured to engage the compressed gas cartridge in response to the applied force, wherein the piercing element is configured to release a compressed gas into the compression chamber to push on the plunger head to provide extrusion assistance, the pressure bleed orifice is configured to allow the released compressed gas to bleed from the compression chamber, and axial movement of the plunger stem relative to the syringe body is configured to change an amount by which the plunger stem partially blocks the opening to change an amount of the extrusion assistance.

13. The compressed gas assisted syringe of claim 12, wherein the pressure bleed orifice is disposed on a lateral side of the syringe body.

14. The compressed gas assisted syringe of claim 12, wherein the syringe body is elongated in a longitudinal direction, wherein the pressure bleed orifice is longer in the longitudinal direction than in a circumferential direction relative to the syringe body.

15. The compressed gas assisted syringe of claim 14, wherein the pressure bleed orifice has a generally rectilinear shape extending in the longitudinal direction.

16. A compressed gas assisted syringe comprising:

a syringe body comprising a material cavity, a compression chamber, and a pressure bleed orifice;

a plunger head disposed proximal to the syringe body and configured to receive an applied force;

a plunger stem extending distally from the plunger head into the syringe body, the plunger stem comprising a cartridge chamber configured to house a compressed gas cartridge; and a piercing element disposed in the syringe body and configured to engage the compressed gas cartridge in response to the applied force, wherein the piercing element is configured to release a compressed gas into the compression chamber to push on the plunger head to provide extrusion assistance, the pressure bleed orifice being configured to allow the released compressed gas to bleed from the compression chamber, and wherein a first opening percentage of the pressure bleed orifice is configured to provide a first amount of the extrusion assistance by allowing the released compressed gas to bleed from the compression chamber at a first rate, and a second opening percentage of the pressure bleed orifice greater than the first opening percentage is configured to provide a second amount of the extrusion assistance less than the first amount by allowing the released compressed gas to bleed from the compression chamber at a second rate greater than the first rate.

* * * * *